US00PP18122P2

(12) United States Plant Patent
Ishihara et al.

(10) Patent No.: US PP18,122 P2
(45) Date of Patent: Oct. 9, 2007

(54) ***PETUNIA* PLANT NAMED 'SUNSURFCOPASAKU'**

(50) Latin Name: ***Petunia hybrida* Vilm.**
Varietal Denomination: Sunsurfcopasaku

(75) Inventors: Takuro Ishihara, Tokyo (JP); Kazunari Iwaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/444,074

(22) Filed: May 31, 2006

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *petunia* plant particularly distinguished by medium-size, single, light-pink flowers, abundant branching with a great profusion of blooms, excellent tolerance to low temperatures, and a compact, mounding growth habit is disclosed.

2 Drawing Sheets

Genus and species: *Petunia hybrida* Vilm.
Variety denomination: 'Sunsurfcopasaku'.

BACKGROUND OF THE NEW PLANT

The present invention comprises a new and distinct cultivar of *petunia,* botanically known as *Petunia hybrida* Vilm., and hereinafter referred to by the cultivar name 'Sunsurfcopasaku'. The new cultivar originated from a hybridization made in June 2002 in Higashiomi, Shiga, Japan. The female parent was a cultivar *petunia* plant 'Fantasy Pink' (unpatented), while the male parent was a proprietary *petunia* plant 'P01-531' (unpatented).

The new cultivar was created in 2002 in Higashiomi, Shiga, Japan and has been asexually reproduced repeatedly by vegetative cuttings in Higashiomi, Shiga, Japan. The present invention has been found to retain its distinctive characteristics through successive asexual propagations.

SUMMARY OF THE INVENTION

The following are the most outstanding and distinguishing characteristics of this new cultivar when grown under normal horticultural practices in Higashiomi, Shiga, Japan.

A) Single, medium-size, light-pink flowers;

B) Abundant branching with a great profusion of blooms;

C) Compact and mounding plant habit;

D) Whole plant remains in bloom for a considerable period of time; and

E) Excellent tolerance to low temperatures.

DESCRIPTION OF PHOTOGRAPHS

This new *petunia* plant is illustrated by the accompanying photographs which show blooms and foliage of the plant in full color, the colors shown being as true as can be reasonably obtained by conventional photographic procedures. The photographs are of a 4-month-old plant grown in a greenhouse in Higashiomi, Shiga, Japan.

DESCRIPTION OF THE NEW CULTIVAR

Figure 1:
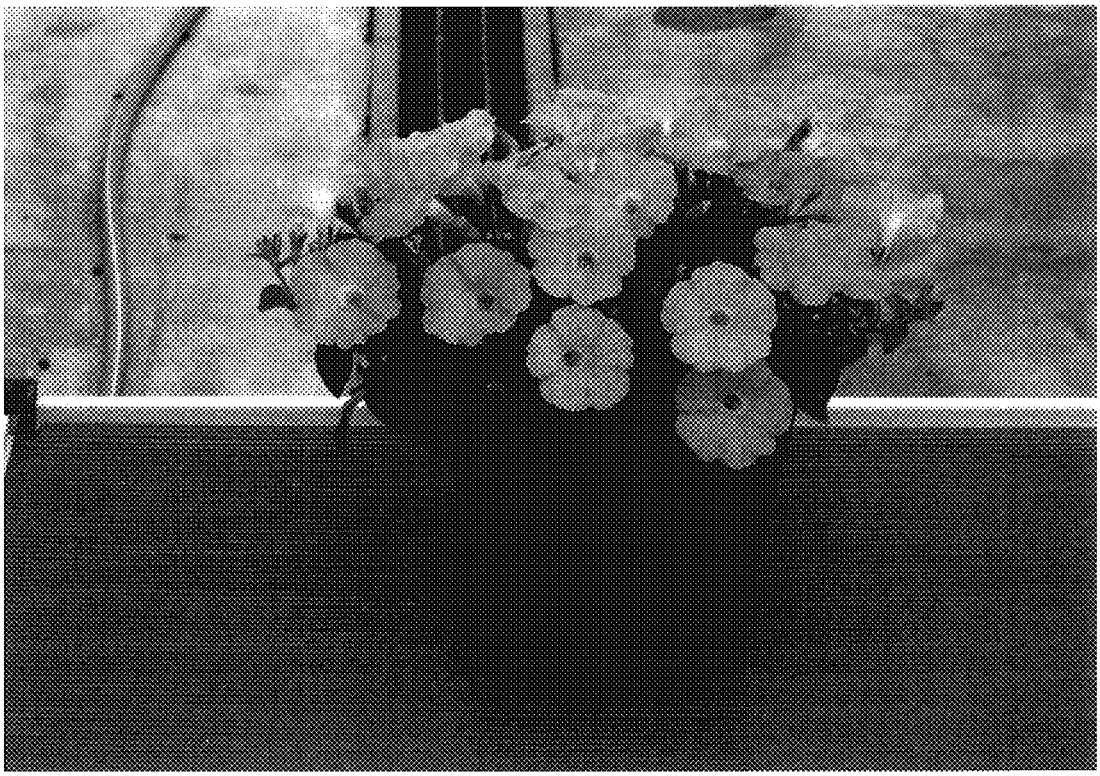
FIG. 1 shows the overall plant habit, including blooms, buds and foliage.
Figure 2:
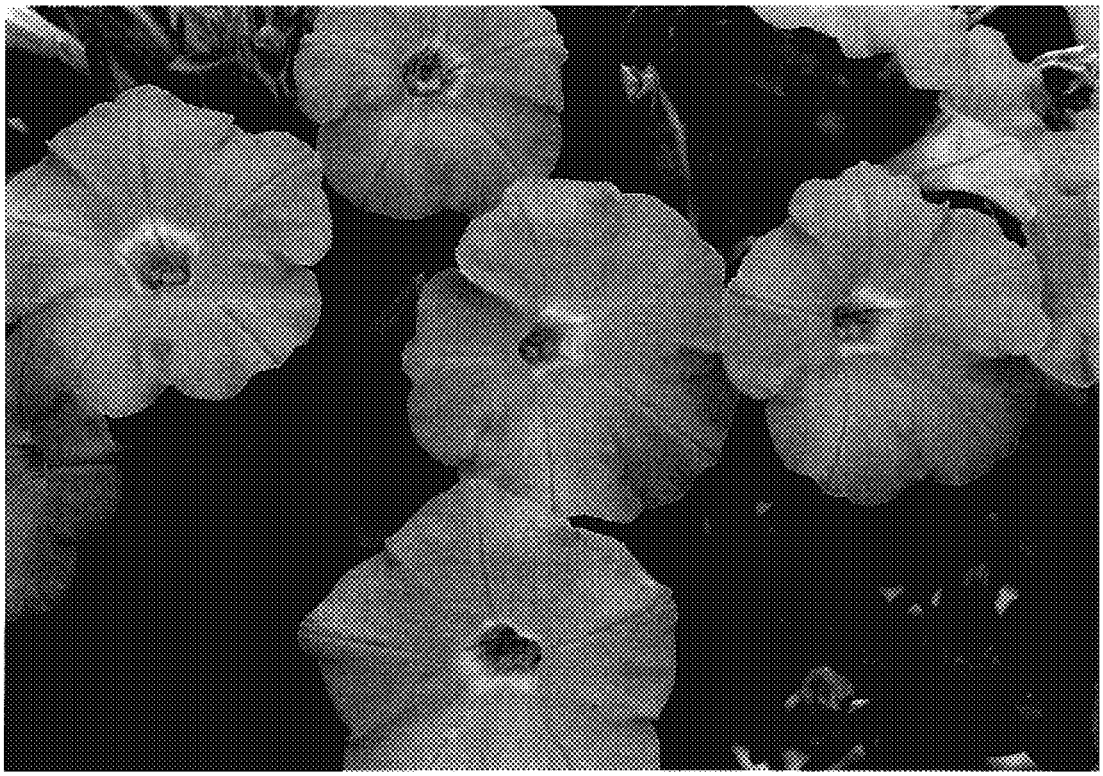
FIG. 2 shows mature flowers.

The following detailed description sets forth the distinctive characteristics of 'Sunsurfcopasaku'. The data which define these characteristics were collected from asexual reproductions carried out in Higashiomi, Shiga, Japan. The plant history was taken on 4-month old plants which were planted as rooted cuttings in 15-cm pots in 2005 and grown in a greenhouse between 13° C. and 23° C. The plants were pinched once in April 2005. Observations were made when the plants were in full flower in June 2005. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
- *Family.*—Solanaceae.
- *Botanical.*—*Petunia hybrida* Vilm.
- *Common name.*—*Petunia.*

Parentage:
- *Female parent.*—'Fantasy Pink', a cultivar vivid-pink-flowered *petunia* plant (unpatented).
- *Male parent.*—'P01-531', a proprietary light-pink-flowered *petunia* plant (unpatented).

Growth:
- *Form.*—Annual.
- *Habit.*—Compact and mounding, freely branching, vigorous.
- *Height* (*measured from the top of the soil*).—13.8 cm.
- *Diameter or area of spread.*—28.2 cm.
- *Propagation.*—Terminal tips for cutting.
- *Time to produce a finished flowering plant.*—About 14 days, in April to late October, for a 15-cm pot.
- *Keeping quality.*—210 days.
- *Outdoor plant performance.*—Use in containers, pots and landscaping; tolerates temperatures to below 5° C.
- *Time to initiate and develop roots.*—7 days at 20° C. to 25° C.
- *Time to produce rooted cutting or liner* (*young plant*).—21 days at 20° C. to 25° C.
- *Root description.*—Light brown, fibrous, fine; fleshy, freely-branching.

Branches:
*Number of branches.*—6 basal branches; 20 lateral branches.
*Length of lateral branches.*—12.8 cm.
*Diameter of lateral branches.*—0.19 cm.
Stems:
*Description.*—Round in cross-section.
*Color.*—RHS 144A.
*Stem length.*—12.8 cm.
*Diameter.*—0.19 cm.
*Internode length.*—1.1 cm.
*Anthocyanin.*—Absent.
*Texture.*—Pubescent.
Leaves:
*Arrangement.*—Alternate, single leaves, 20 leaves per lateral branch.
*Apex.*—Acute.
*Base.*—Rounded.
*Color (mature leaves).*—Upper surface: RHS 137C. Lower surface: RHS 146C.
*Color (immature leaves).*—Upper surface: RHS 137C. Lower surface: RHS 146C.
*Margin.*—Entire.
*Size.*—Length: 3.5 cm. Width: 1.7 cm.
*Shape.*—Ovate.
*Texture.*—Pubescent on both sides.
*Venation.*—Type: Reticulate. Color (both surfaces): RHS 145B.
*Petiole.*—Length: 0.5 cm. Diameter: 0.08 cm. Color: RHS 144D. Texture: Pubescent.
Flower buds:
*Color.*—RHS 151C; at apex RHS 199B.
*Shape.*—Cylindrical.
*Size.*—Length: 3.1 cm. Diameter: 0.41 cm.
Inflorescence:
*Blooming habit.*—Continuous from Spring to Fall.
*Inflorescence type.*—Single flower, self-cleaning.
*Arrangement.*—Borne in upper leaf axils.
*Aspect.*—Upright to outward.
*Shape.*—Single, salverform.
*Fragrance.*—Absent.
*Flower number (per inflorescence).*—One.
*Quantity of flowers and buds per plant.*—99.
*Flower longevity on plant.*—5 days.
*Peduncle.*—Color: RHS 144A. Length: 3.2 cm. Diameter: 0.11 cm. Texture: Pubescent, viscid. Angle: Outward.
Flowers:
*Size.*—Height (flower depth): 4.3 cm. Diameter: 4.4 cm.
*Corolla tube.*—Shape: Tube. Length: 3.0 cm. Diameter (proximal end): 0.27 cm. Color (outside): RHS 155A with RHS 183C venation. Texture: Pubescent.
*Petals.*—Arrangement: Single whorl. Shape: Very broadly obovate, fused. Quantity: 5. Size: Length (from the throat): 2.1 cm. Width: 2.2 cm. Apex: Truncate. Base: Fused. Margin: Entire, weakly undulated. Color (when opening): Upper surface: RHS N74B. Lower surface: RHS 69C. Color (fully opened): Upper surface: RHS N74C. Lower surface: RHS 69C. Throat color (inside): RHS 155A with RHS 183C venation. Throat diameter (distal end): 0.82 cm. Petal texture (both surfaces): Smooth, satiny.
*Calyx.*—Form: Tubular, star-shape, single whorl. Length: 1.3 cm. Diameter: 1.5 cm.
*Sepals.*—Arrangement: Single whorl. Number: 5. Shape: Narrow, elliptic. Apex: Obtuse. Base: Fused. Margin: Entire. Size: Length: 1.0 cm. Width: 0.2 cm. Color (mature): RHS 137B (both surfaces). Color (immature): RHS 137B (both surfaces).
Reproductive organs:
*Stamens.*—Quantity: 5. Filament: Length: 1.5 cm to 2.0 cm. Color: RHS 145C. Anther: Shape: Ellipsoidal. Size: Length: 0.11 cm. Width: 0.11 cm. Color: RHS 11C.
*Pollen.*—Amount: Scarce. Color: RHS 19D.
*Pistil.*—Quantity: One. Length: 1.96 cm.
*Style.*—Length: 1.7 cm. Color: RHS 144D.
*Stigma.*—Shape: Transversely ellipsoidal. Color: RHS 144A.
*Ovary color.*—RHS 144A.
Fruit and seed set: Seed production has not been observed.
Disease and insect resistance: No particular resistance or susceptibility to diseases or insects noted to date.

COMPARISON WITH PARENTAL AND COMMERCIAL CULTIVARS

'Sunsurfcopasaku' differs from the female parent 'Fantasy Pink' (unpatented), by having light-pink flowers, while 'Fantasy Pink' has vivid-pink flowers. Additionally, 'Sunsurfcopasaku' has a larger flower diameter and a mounding plant habit, while 'Fantasy Pink' has a smaller flower diameter and an upright plant habit.

'Sunsurfcopasaku' differs from the male parent 'P01-531' (unpatented), by having a taller plant height and a mounding plant habit, while 'P01-531' has a shorter plant height and a decumbent plant habit.

'Sunsurfcopasaku' is similar to the commercial variety 'Suncopablue' (U.S. Plant Pat. No. 16,355) however, there are differences as listed in Table 1 below:

TABLE 1

Comparison of Characteristics between 'Sunsurfcopasaku' and 'Suncopablue'

| Characteristic | 'Sunsurfcopasaku' | 'Suncopablue' |
|---|---|---|
| Growth Habit | Mounding | Decumbent |
| Plant diameter | 28.2 cm | 34.6 cm |
| Internode length | 1.1 cm | 2.1 cm |
| Leaf Shape | Ovate | Elliptic |
| Leaf Apex | Acute | Acute |
| Leaf width | 1.7 cm | 2.2 cm |
| Leaf color (mature) | Upper surface: RHS 137C | Upper surface: RHS 144B |
| Flower height | 4.3 cm | 3.0 cm |
| Petal apex shape | Truncate | Rounded |
| Petal color (fully opened) | Upper surface: RHS N74C<br>Lower surface: RHS 69C | Upper surface: RHS N87A<br>Lower surface: RHS N87C |
| Throat color (inside) | RHS 155A with RHS 183C venation | RHS N81C |
| Corolla tube color (outside) | RHS 155A with RHS 183C venation | RHS 83B |
| Calyx length | 1.3 cm | 1.0 cm |
| Peduncle length | 3.2 cm | 1.8 cm |
| Anther color | RHS 11C | RHS 150D |
| Amount of pollen | Scarce | Normal |
| Stigma color | RHS 144A | RHS 15C |

We claim:

1. A new and distinct cultivar of *petunia* plant as shown and described herein.

* * * * *